United States Patent [19]

Kleiner et al.

[11] Patent Number: 5,502,261
[45] Date of Patent: Mar. 26, 1996

[54] PROCESS FOR PREPARING 2,2'-BIS(HALOMETHYL)-1,1'-BINAPHTHYL

[75] Inventors: Hans-Jerg Kleiner, Kronberg; Dieter Regnat, Eppstein; Horst Röschert, Ober-Hilbersheim, all of Germany

[73] Assignee: Hoechst Aktiengesellschaft, Frankfurt

[21] Appl. No.: 408,057

[22] Filed: Mar. 21, 1995

[30] Foreign Application Priority Data

Mar. 23, 1994 [DE] Germany .................. 44 09 974.6
Sep. 19, 1994 [DE] Germany .................. 44 33 296.3

[51] Int. Cl.[6] .................. C07C 17/14; C07C 22/04
[52] U.S. Cl. .................. 570/196; 570/191; 570/197
[58] Field of Search .................. 570/190, 196, 570/206, 191, 197

[56] References Cited

U.S. PATENT DOCUMENTS 4,329,525  5/1982  Riegel et al. .................. 570/191
4,489,210  12/1984  Judat et al. .................. 568/779
4,950,817  8/1990  Botta et al. .................. 570/208
4,967,026  10/1990  Daren .................. 570/194

FOREIGN PATENT DOCUMENTS 0612707  8/1994  European Pat. Off. .

OTHER PUBLICATIONS

Tetrahedron Letters, vol. 30, No. 27 (1989), Binaphthylcyclopentadiene: A $C_2$-Symmetric Annulated Cyclopentadienyl Ligand with Axial Chirality, pp. 3513–3516.

*Primary Examiner*—Werren B. Lone
*Attorney, Agent, or Firm*—Connolly & Hutz

[57] ABSTRACT

The present invention relates to a process for preparing 2,2'-bis(halomethyl)-1,1'-binaphthyl, by reacting 2,2'-dimethyl-1,1'-binaphthyl in the presence of a solvent with a halogenating agent under the action of light having a wavelength of from $10^{-5}$ to $10^{-8}$ m in the presence or absence of a free-radical former at from −10 to 120° C.

26 Claims, No Drawings

PROCESS FOR PREPARING 2,2'-BIS(HALOMETHYL)-1,1'-BINAPHTHYL

The present invention relates to an improved process for preparing 2,2'-bis(halomethyl)-1,1'-binaphthyl, in particular 2,2'-bis(chloromethyl)-1,1'-binaphthyl and 2,2'-bis(bromomethyl)-1,1'-binaphthyl.

2,2'-Bis(halomethyl)-1,1'-binaphthyls represent, as bifunctional derivatives, valuable starting materials for preparing a large number of further organic compounds. They can, for example, be converted by customary reactions with replacement of the halogen atom into the corresponding alcohols, nitriles or amines. These materials are, as bifunctional compounds, in turn suitable, on the one hand, as building blocks for preparing plastics such as polyethers, polyesters, epoxy resins or polyurethanes and, on the other hand, as components for lubricants, additives, stabilizers or antioxidants.

2,2'-Bis(halomethyl)-1,1'-binaphthyls can also be used directly for preparing organophosphorus compounds.

Thus, 2,2'-bis(bromomethyl)-1,1'-binaphthyl can be used as starting material for preparing 2,2'-bis(diphenylphosphinylmethyl)-1,1'-binaphthyl. Pure 2,2'-bis(bromomethyl)-1,1'-binaphthyl is reacted with methyl diphenylphosphinite to give, as described in JP 7 939 059 or CA 91,91764 v, 2,2'-bis(diphenylphosphinylmethyl)-1,1'-binaphthyl. Reduction of this product can be used to prepare 2,2'-bis(diphenylphosphinomethyl)-1,1'-binaphthyl, a bidentate phosphine (phosphane). This bidentate phosphine is used as a ligand for catalysts, for example in the coupling of haloaromatics catalyzed by metal complexes.

2,2'-Bis(chloromethyl)-1,1'-binaphthyl is prepared by reacting 2,2'-bis(bromomethyl)-1,1'-binaphthyl in dimethylformamide with an excess of lithium chloride, with chlorine-bromine exchange occurring (Chong et al., J. Org. Chem. 58 (1993), 1266). This process is complicated (dimethylformamide as solvent, workup in water) and, in addition, starts with a material which is already dihalogenated, namely the corresponding dibrominated product. This starting material is not readily obtainable. Furthermore, the reaction leads to waste products containing lithium chloride and lithium bromide, which lead to difficulties in the workup and present problems in disposal.

To prepare 2,2'-bis(bromomethyl)-1,1'-binaphthyl, the starting material used is 2,2'-dimethyl-1,1'-binaphthyl and the methyl groups are brominated using N-bromosuccinimide to give 2,2'-bis(bromomethyl)-1,1'-binaphthyl. In this reaction, which has been described a number of times in the literature and is carried out in the presence of a free-radical former at the boiling point but without the action of light, tetrachloromethane is generally used as solvent (M. E. Jung et al., Tetrahedron Lett. 29 (1988) 6199; H. J. Bestmann et al., Chem. Ber. 107 (1974) 2926; J. P. Mazaleyrat, Chem. Commun. 1985, 317; T. Hayashi et al., J. Am. Chem. Soc. 110 (1988) 8153.

Owing to the comparatively low boiling point of tetrachloromethane, which is 76.5° C., reaction at higher temperatures can only be carried out under pressure which is technically more complicated. In addition, the yield of 2,2'-bis(bromomethyl)-1,1'-binaphthyl is, at about 60%, not very high.

The unpublished European Patent Application EP 93 116 788.6, which goes back, inter alia, to the unpublished German Patent Application P 43 08 562.8, describes the preparation of 2,2'-bis(bromomethyl)-1,1'-binaphthyl by reaction of 2,2'-dimethyl-1,1'-binaphthyl with N-bromosuccinimide in the presence of benzoyl peroxide, but without the action of light, in boiling chlorobenzene (boiling point: 132° C.). After the reaction is complete, the solvent is evaporated, the residue is taken up in ethyl acetate and washed first with 10% strength $Na_2SO_3$ solution, then with saturated $Na_2CO_3$ solution and finally with saturated NaCl solution. After drying and recrystal-lization, the yield is 65%. However, this process proves to be complicated (evaporation of the solvent, transfer of the residue into another solvent and triple washing each time with an aqueous sodium salt solution), and in addition the yield also leaves something to be desired.

There is therefore a need to develop a process for preparing 2,2'-bis(halomethyl)-1,1'-binaphthyls which is not restricted only, on the one hand, to the preparation of 2,2'-bis(chloromethyl)-1,1'-binaphthyl or, on the other hand, to the preparation of 2,2'-bis(bromomethyl)-1,1'-binaphthyl, but can also be generally used. It should not have the disadvantages indicated above, be simple and reliable to carry out at comparatively low temperatures and make the desired product available in good yield and with high selectivity.

This object is achieved by a process for preparing 2,2'-bis(halomethyl)-1,1'-binaphthyl. It comprises reacting 2,2'-dimethyl-1,1'-binaphthyl in the presence of a solvent with a halogenating agent under the action of light having a wavelength of from $10^{-5}$ to $10^{-8}$ m in the presence or absence of a free-radical former at from −10° to 120° C.

From the course of reaction of halogenations of organic compounds it is known that a halogenation in the side chain of an aromatic is customarily carried out at quite high temperatures (boiling point) in the presence of light (sunlight), while the halogenation of the ring is carried out at low temperatures using a catalyst.

In view of this background, it must be regarded as surprising that the halogenation of the invention under the action of light leads, even at comparatively low to very low temperatures, not to any significant extent to a halogenation of the aromatic ring, but with high selectivity to a halogenation of the methyl groups, i.e. the side chain, in the 2,2'-dimethyl-1,1'-binaphthyl. However, account must here be taken of the fact that the temperature selected in each case is also dependent on the reactivity of the respective halogenating agent. A relatively unreactive halogenating agent, for example N-chlorosuccinimide, will require a higher reaction temperature than a comparatively reactive halogenating agent such as chlorine, bromine or N-bromosuccinimide.

In general, the amount of solvent used is of no great importance. However, enough should be used. In general, it is sufficient to use 2,2'-dimethyl-1,1'-binaphthyl and the solvent in a weight ratio of 1:(3 to 40), in particular 1:(4 to 20), preferably 1:(5 to 15).

The solvent used is usually one which is inert or very largely inert to the reaction conditions, i.e. to the action of the halogenating agent under the reaction conditions.

The solvent used can be a monochlorinated or polychlorinated benzene, a monochlorinated or polychlorinated aliphatic hydrocarbon, an ester of an aliphatic carboxylic acid having from 1 to 6 carbon atoms and an aliphatic alcohol having from 1 to 4 carbon atoms or a mixture of the same.

Suitable solvents are, for example, chloroform, tetrachloromethane, dichloromethane, chlorobenzene, ortho-, meta- and para-dichlorobenzene, methyl formate, ethyl formate, methyl acetate, ethyl acetate, propyl acetate, butyl acetate, methyl propionate, ethyl propionate, propyl propionate, butyl propionate, methyl butyrate, ethyl butyrate, propyl butyrate and butyl butyrate. Mixtures of these solvents can also be used. Well suited solvents are chlorobenzene and/or dichlorobenzene. Chlorobenzene is particularly suitable. In some cases, esters of the abovementioned type, in particular methyl and ethyl esters of aliphatic carboxylic acids having from 1 to 3 carbon atoms, can also be used with good results.

Usually, 2,2'-dimethyl-1,1'-binaphthyl and the halogenating agent are used in a molar ratio of 1:(1.5 to 2.5). In many cases, it is sufficient to use 2,2'-dimethyl-1,1'-binaphthyl and the halogenating agent in a molar ratio of 1:(1.8 to 2.3), preferably 1:(1.9 to 2.2).

The halogenation agent used can be a chlorinating agent or a brominating agent. The customary chlorinating agents or brominating agents can be used. Examples of such halogenating agents are chlorine, N-chlorosuccinimide, bromine, N-bromosuccinimide, 1,3-dibromo-5,5-dimethylhydantoin or brominated Meldrum's acid.

In a series of cases, it has been found to be useful to use N-chlorosuccinimide or N-bromosuccinimide as halogenating agent.

If N-chlorosuccinimide or N-bromosuccinimide is used as halogenating agent, succinimide is formed in each case as reaction product during the course of the halogenation, both from the N-chlorosuccinimide and from the N-bromosuccinimide. The succinimide can, if desired after cooling the solution containing the reaction mixture, be removed by filtration. Another possibility is to remove the succinimide formed by extraction with water. Usually from 10 to 100% by weight of water, based on the reaction mixture, are used for this purpose.

A particularly simple and at the same effective method of removing succinimide is to separate off the succinimide formed from the reaction mixture in a first step by filtration and in a second step by extraction with water. Here, comparatively little water is used and, accordingly, little wastewater is obtained.

The process of the invention is carried out under the action of light. The light source can be a customary UV irradiator, for example a daylight lamp, a doped or undoped mercury vapor lamp or low-pressure mercury vapor lamp.

These light sources have a spectrum from $10^{-5}$ to $10^{-8}$ m, in particular from $10^{-6}$ to $2\times10^{-7}$ m. These ranges include the light components, in particular UV components, required for the reaction.

If desired, the reaction of 2,2'-dimethyl-1,1'-binaphthyl with the halogenating agent can also be carried out in the presence of a free-radical former. It has been actually found that in some cases the addition of a free-radical former (free-radical initiator) can have a favorable effect in addition to the action of light. Suitable free-radical formers are the customary free-radical formers for a free-radical halogenation, for example organic peroxides, organic percarboxylic acids, organic hydroperoxides or organic azo compounds. Examples of suitable free-radical formers are benzoyl peroxide, benzoyl perhexadecanoate and azobisisobutyronitrile.

Unreacted free-radical formers can be removed, for example by scrubbing with an aqueous $Na_2SO_3$ solution.

The free-radical formers are used in customary amounts. In general, it is sufficient to use them in an amount of from 0.1 to 5% by weight, in particular from 0.5 to 2% by weight, based on 2,2'-dimethyl-1,1'-binaphthyl to be reacted.

As already mentioned in the introduction, the halogenation is carried out at from −10° to 120° C. In many cases it has been found to be sufficient to allow the halogenation to proceed at from −5° to 100° C., in particular from 0° to 80° C.

In connection with this, attention is drawn to the fact that the reaction temperature at which the halogenation is to take place also depends to a not inconsiderable extent on the halogenating agent used. A comparatively unreactive halogenating agent will react with the 2,2'-dimethyl-1,1'-binaphthyl only at higher temperatures than a comparatively reactive halogenating agent.

If a chlorinating agent is used as halogenating agent, it is advisable to carry out the reaction at from 25° to 120° C., in particular from 50° to 100° C. When using N-chlorosuccinimide, which is comparatively unreactive, the reaction is carried out at from 5° to 120° C., in particular from 70° to 100° C.

If a brominating agent is used as halogenating agent, the process of the invention can be carried out at comparatively quite low temperatures. In general, it is sufficient to carry out the bromination at from −10° to 80° C. For many cases, reaction temperatures of from −5° to 50° C., in particular from 0° to 40° C., are found to be sufficient.

If bromine is used as halogenating agent, it is advisable to carry out the reaction at from 10° to 80° C., in particular from 25° to 75° C., preferably from 35° to 70° C. When using N-bromosuccinimide, the halogenation can be carried out with good results at from −10° to 50° C., in particular from −5° to 40° C., preferably from 0° to 30° C.

For any further processing of the reaction mixture obtained after the halogenation, it may be desirable to replace the solvent originally used in the halogenation stage by a further solvent. This is necessary, in particular, when the original solvent does not behave as inert under the conditions of further processing, for example under the action of basic materials. In this case, the reaction mixture after halogenation has added to it a further solvent which boils at a higher temperature than the solvent originally used and the solvent originally used is subsequently distilled off as desired and needed, completely or partially.

Suitable further solvents are aromatic hydrocarbons, for example toluene, o-xylene, m-xylene, p-xylene, mixtures of these xylenes, ethylbenzene and/or mesitylene, and high-boiling aliphatic hydrocarbons, for example petroleum ether having a boiling point>100° C., decalin, ligroin and/or isooctane. If the solvent exchange is to be carried out in a particularly gentle manner, the solvent originally used can be distilled off as an azeotrope and/or under reduced pressure.

If it is intended that the 2,2'-bis(halomethyl)-1,1'-binaphthyl be isolated as a pure product, any succinimide formed is removed, as described above, by filtration and extraction with water, the reaction mixture is dried and filtered off from the drying agent. The solvent originally used is subsequently removed under reduced pressure. For the isolation of 2,2'-bis(bromomethyl)-1,1'-binaphthyl in pure form, owing to the thermal lability of the reaction mixture which begins to decompose at temperatures above 50° C., the removal of the solvent originally used should be carried out at a liquid phase temperature<50° C. In the isolation of 2,2'-bis(chloromethyl)-1,1'-binaphthyl in pure form, the solvent originally used can be removed at higher temperatures, for example up to about 70° C., without appreciable problems occurring. The remaining crude product, which usually has an oily consistency, is taken up in a solvent, for example toluene, o-xylene, m-xylene, p-xylene or a mixture of these solvents, and is purified by recrystallization.

The following examples illustrate the invention, without limiting it.

Experimental part

EXAMPLE 1

Preparation of 2,2'-bis(chloromethyl)-1,1'-binaphthyl

With exclusion of moisture, 282.4 g (1.0 mol) of 2,2'-dimethyl-1,1'-binaphthyl and 280.4 g (2.1 mol) of N-chlorosuccinimide are suspended in 1.7 l of chlorobenzene in a 4 l glass flask and are illuminated for 16 hours at 70° C. using a UV immersion lamp. The precipitated succinimide is filtered off, the solution is extracted twice with 200 ml of water each time, dried using sodium sulfate, filtered and concentrated in vacuo. This gives 350.0 g of yellowish brown oil having a composition (gas-chromatographic analysis in mol %) of 55% of 2,2,-bis(chloromethyl)-1,1'-binaphthyl, 28% of 2-chloromethyl-2'-methyl-1,1'-binaphthyl and 10% of 2-dichloromethyl-2'-chloromethyl-1,1'-binaphthyl and 7% of products which were not identified in more detail.

The conversion is, based on 2,2'-dimethyl-1,1'-binaphthyl used, 100%, the yield of 2,2'-bis(chloromethyl)-1,1'-binaphthyl is 55%, based on 2,2'-dimethyl-1,1'-binaphthyl used.

Comparative Experiment 1a

Preparation of 2,2'-bis(chloromethyl)-1,1'-binaphthyl without action of light With exclusion of moisture, 282.4 g (1.0 mol) of 2,2'-dimethyl-1,1'-binaphthyl, 280.4 g (2.1 mol) of N-chlorosuccinimide and 500 mg of benzoyl peroxide are suspended in 1.7 l of chlorobenzene in a 4 l glass flask and stirred for 16 hours under reflux (132° C.). The precipitated succinimide is filtered off, the solution extracted twice with 200 ml of water each time and once with 100 ml of $Na_2SO_3$ solution, dried using sodium sulfate, filtered and concentrated in vacuo. This gives 354.0 g of a yellowish brown oil having a composition (gas-chromatographic analysis in mol %) of 38% of 2,2'-bis-(chloromethyl)-1,1'-binaphthyl, 35% of 2-chloromethyl-2'-methyl-1,1'-binaphthyl and 8% of 2-dichloromethyl-2'-chloromethyl-1,1'-binaphthyl.

The conversion is, based on 2,2'-dimethyl-1,1'-binaphthyl used, 96%, the yield of 2,2'-bis(chloromethyl)-1,1'-binaphthyl is 37%, based on 2,2'-dimethyl-1,1'-binaphthyl used.

Comparative Experiment 1b

Preparation of 2,2'-bis(chloromethyl)-1,1'-binaphthyl under the action of light, but at 30° C.

With exclusion of moisture, 282.4 g (1.0 mol) of 2,2'-dimethyl-1,1'-binaphthyl and 280.4 g (2.1 mol) of N-chlorosuccinimide are suspended in 1.7 l of chlorobenzene in a 4 l glass flask and illuminated for 16 hours at 130° C. using a UV immersion lamp. The precipitated succinimide is filtered off, the solution is extracted twice with 200 ml of water each time, dried using sodium sulfate, filtered and concentrated in vacuo. This gives 354.0 g of a yellowish brown oil having a composition (gas-chromatographic analysis in mol %) of 47% of 2,2'-bis(chloromethyl)-1,1'-binaphthyl, 22% of 2-chloromethyl-2'-methyl-1,1'-binaphthyl and 12% of 2-dichloro-methyl-2'-chloromethyl-1,1'-binaphthyl and 19% of products which were not identified in more detail.

The conversion is, based on 2,2'-dimethyl-1,1'-binaphthyl used, 100%, the yield of 2,2'-bis(chloromethyl)-1,1'-binaphthyl is 47%, based on 2,2'-dimethyl-1,1'-binaphthyl used.

Comparative Experiment 1c

Preparation of 2,2'-bis(chloromethyl)-1,1'-binaphthyl without action of light (similar to Example 1, but using free-radical formers)

With exclusion of moisture, 282.4 g (1.0 mol) of 2,2'-dimethyl-1,1'-binaphthyl, 280.4 g (2.1 mol) of N-chlorosuccinimide and 500 mg of benzoyl peroxide are suspended in 1.7 l of chlorobenzene in a 4 l glass flask and stirred for 16 hours at 70° C. A sample is then taken and is worked up as described in Comparative Experiment 1a. According to gas-chromatographic analysis (in mol %) of the reaction mixture formed, the conversion is, based on 2,2'-dimethyl-1,1'-binaphthyl used, 40%, the yield of 2,2'-bis(chloromethyl)-1,1'-binaphthyl is 18%, based on 2,2'-dimethyl-1,1'-binaphthyl used.

EXAMPLE 2

Preparation of 2,2'-bis(bromomethyl)-1,1'-binaphthyl

With exclusion of moisture, 282.4 g (1 mol) of 2,2'-dimethyl-1,1'-binaphthyl and 373.9 g (2.1 mol) of N-bromosuccinimide are admixed with 1.7 l of chlorobenzene in a 4 l glass flask and illuminated while stirring for 8 hours at from 5° to 10° C. using a UV immersion lamp. The precipitated succinimide is filtered off, the solution extracted with 200 ml of water each time, dried using sodium sulfate and filtered. It is subsequently concentrated in vacuo at from 20° to 30° C. and gives 440 g of a yellowish brown oil containing 80±2 mol % of 2,2'-bis(bromomethyl)-1,1'-binaphthyl. Crystallization from toluene gives 308 g of colorless crystals having a melting point of from 146° to 149° C. The conversion is, based on 2,2'-dimethyl-1,1'-binaphthyl used, 100%, the yield of 2,2'-bis(bromomethyl)-1,1'-binaphthyl isolated is 70%, based on 2,2'-dimethyl-1,1'-binaphthyl used.

Comparative Experiment 2

Preparation of 2,2'-bis(bromomethyl)-1,1'-binaphthyl without action of light in accordance with DE 43 08 562.8

A mixture of 10.7 g (60 mmol) of N-bromosuccinimide and 100 mg of benzoyl peroxide is added in portions to 8.5 g (30 mmol) of 2,2'-dimethyl-1,1'-binaphthyl in 100 ml of chlorobenzene under reflux at the boiling point (132° C.). After addition is complete, the mixture is stirred for a further 1 hour at the boiling point and the solvent is evaporated. The residue is taken up in 50 ml of ethyl acetate and washed once with each of 10% strength $Na_2SO_3$ solution, saturated $Na_2SO_3$ solution and saturated NaCl solution. After drying using $MgSO_4$, the solution is concentrated. This gives 13.2 g of yellow oil. Crystallization from toluene gives 8.6 g of colorless crystals having a melting point of 147°–149° C. The conversion is, based on 2,2'-dimethyl-1,1'-binaphthyl used, 100%, the yield of 2,2'-bis(bromomethyl)-1,1'-binaphthyl isolated is 65%, based on 2,2'-dimethyl-1,1'-binaphthyl used.

EXAMPLE 3

Preparation of 2,2'-bis(bromomethyl)-1,1'-binaphthyl

With exclusion of moisture and under a nitrogen blanket, 282.4 g (1.0 mol) of 2,2'-dimethyl-1,1'-binaphthyl are dissolved in 2.5 l of chlorobenzene in a 4 l glass flask fitted with a downstream alkaline waste air scrubber. At 25° C. and under illumination using a UV immersion lamp, 383.5 g (2.4 mol) of bromine are added dropwise in such a way that the reaction solution is immediately decolorized again (duration: from 2 to 3 hours). After a total illumination time of 5 hours, the solution is extracted successively twice with 500 ml each time of half-saturated $NaHCO_3$ solution and once with 500 ml of water, dried using sodium sulfate, filtered and concentrated in vacuo. This gives 440.0 g of yellowish brown oil having a composition (gas-chromatographic analysis in mol %) of 65% of 2,2'-bis(bromomethyl)-1,1'-binaphthyl, 12% of 2-bromomethyl-2'-methyl-1,1'-binaphthyl and 10% of 2-dibromomethyl-2'-bromomethyl-1,1'-binaphthyl.

The conversion is, based on 2,2'-dimethyl-1,1'-binaphthyl used, 100%, the yield of 2,2'-bis(bromomethyl)-1,1'-binaphthyl is 65%, based on 2,2'-dimethyl-1,1'-binaphthyl used.

We claim:

1. A process for preparing 2,2-bis(halomethyl)-1,1'-binaphthyl, which comprises the step of reacting 2,2'-dimethyl-1,1'-binaphthyl in the presence of a solvent with a halogenating agent under the action of light having a wavelength of from $10^{-5}$ to $10^{-8}$ m at from −10° to 120° C.

2. The process as claimed in claim 1, wherein 2,2'-dimethyl-1,1'-binaphthyl and the solvent are used in a weight ratio of 1: (3 to 40).

3. The process as claimed in claim 1, wherein 2,2'-dimethyl-1,1'-binaphthyl is reacted in a solvent which is inert to the reaction conditions.

4. The process as claimed in claim 1,
wherein the solvent is a monochlorinated or polychlorinated benzene, a monochlorinated or polychlorinated aliphatic hydrocarbon, an ester of an aliphatic carboxylic acid having from 1 to 6 carbon atoms and an aliphatic alcohol having from 1 to 4 carbon atoms.

5. The process as claimed in claim 1, wherein the solvent used is dichloromethane, chlorobenzene, dichlorobenzene, or mixtures thereof.

6. The process as claimed in claim 1, wherein the solvent used is chlorobenzene, dichlorobenzene, or a mixture thereof.

7. The process as claimed in claim 1, wherein the solvent used is chlorobenzene.

8. The process as claimed in claim 1, wherein 2,2'-dimethyl-1,1'-binaphthyl and the halogenating agent are used in a molar ratio of 1:(1.5 to 2.5).

9. The process as claimed in claim 1,
wherein the halogenating agent used is a chlorinating agent or brominating agent.

10. The process as claimed in claim 1,
wherein the halogenating agent used is chlorine, N-chlorosuccinimide, bromine, N-bromosuccinimide, 1,3-dibromo-5,5-dimethylhydantoin or brominated Meldrum's acid.

11. The process as claimed in claim 1,
wherein the halogenating agent used is N-chlorosuccinimide, bromine or N-bromosuccinimide.

12. The process as claimed in claim 1, wherein the light source used is UV irradiator.

13. The process as claimed in claim 1,
wherein the free-radical former is an organic peroxide, a peroxycarboxylic acid, an organic hydroperoxide or an organic azo compound.

14. The process as claimed in claim 1,
wherein the free-radical former used is benzoyl peroxide, benzoyl perhexadecanoate or azobisisobutyronitrile.

15. The process as claimed in claim 1, wherein 2,2'-dimethyl-1,1'-binaphthyl is reacted with the halogenating agent at from −5° to 100° C.

16. The process as claimed in claim 1, wherein 2,2'-dimethyl-1,1'-binaphthyl is reacted with a chlorinating agent at from 25° to 120° C.

17. The process as claimed in claim 1, wherein 2,2'-dimethyl-1,1'-binaphthyl is reacted with a brominating agent at from −10° to 80° C.

18. The process as claimed in claim 1, further conducted in the presence of a free-radical former.

19. The process as claimed in claim 1, wherein 2,2'-dimethyl-1,1'-binaphthyl and the solvent are used in a weight ratio of 1:(4 to 20).

20. The process as claimed in claim 1, wherein 2,2'-dimethyl-1,1'-binaphthyl and the solvent are used in a weight ratio of 1:(5 to 15).

21. The process as claimed in claim 1, wherein 2,2'-dimethyl-1,1'-binaphthyl and the halogenating agent are used in a molar ratio of 1:(1.8 to 2.3).

22. The process as claimed in claim 1, wherein 2,2'-dimethyl-1,1'-binaphthyl and the halogenating agent are used in a molar ratio of 1:(1.9 to 2.2).

23. The process as claimed in claim 1, wherein 2,2'-dimethyl-1,1'-binaphthyl is reacted with the halogenating agent at from 0° to 80° C.

24. The process as claimed in claim 1, wherein 2'2'-dimethyl-1,1'-binaphthyl is reacted with a chlorinating agent at a temperature of from 70° to 100° C.

25. The process as claimed in claim 1, wherein 2,2'-dimethyl-1,1'-binaphthyl is reacted with a brominating agent at a temperature of from −5° to 50° C.

26. The process as claimed in claim 1, wherein 2,2'-dimethyl-1,1'-binaphthyl is reacted with a brominating agent at a temperature of from 0° to 40° C.

* * * * *